United States Patent [19]

Bennet

[11] Patent Number: 4,617,317

[45] Date of Patent: Oct. 14, 1986

[54] METHOD OF TREATING ULCERATIVE COLITIS

[76] Inventor: Justin D. Bennet, 4803 Hart Dr., San Diego, Calif. 92116

[21] Appl. No.: 666,753

[22] Filed: Oct. 31, 1984

[51] Int. Cl.$^4$ .......................................... A61K 31/355
[52] U.S. Cl. .................................................. 514/458
[58] Field of Search ........................................ 514/458

[56] References Cited

PUBLICATIONS

Devroede, G.; W. Taylor; W. Sauer; R. Jackman; and G. Stickler. "Cancer Risk and Life Expectancy of Children with Ulcerative Colitis." *The New England Journal of Medicine* (1971, 285: 17–21).

Hill, M., "The Role of Colon Anaerobes in the Metabolism of Bile Acids and Steroids, and its Relation to Colon Cancer." *Cancer*, Dec. Supplement (1975, 36: 2387–2400).

Chem. Abst.—72—219q (1970).
Chem. Abst.—83—(33025d) (1975).
Chem. Abst.—99—(82132a) (1983).

*Primary Examiner*—Stanley J. Friedman
*Attorney, Agent, or Firm*—Brown, Martin, Haller & Meador

[57] ABSTRACT

A method of treating and/or preventing ulcerative colitis in humans by daily administering of between 1–6 grams of biological antagonists of Vitamin K generated either in vivo or in vitro by oxidation of tocopherols.

2 Claims, No Drawings

METHOD OF TREATING ULCERATIVE COLITIS

BACKGROUND OF THE INVENTION

Ulcerative colitis is a chronic, inflammatory disease associated with inflammation of the mucosa of the colon, often starting in the distal portion of the colon, and most frequently affecting individuals ranging in age from 14-40. The most common symptoms are bloody diarrhea accompanied by severe cramps and high fever. Hemorrhage, perforation of the colon, and peripheral arthritis are potential complications. At present neither the cause nor an effective non-surgical method of treating the disease are known. Depending on whether the stage of the disease is classified as mild, moderate, moderately severe, or severe, the strategies for treating it differ. For mild attacks treatment is focused on controlling diarrhea usually with diphenoxylate. Moderate and moderately severe forms of the disease are treated with antibiotics, generally sulfasalazine and/or with corticosteroids respectively. Severe attacks of the disease require hospitalization, drug therapy and in extreme situations colectomy if there is massive hemorrhaging or perforation of the colon. The only known cure for severe ulcerative colitis is complete proctocolectomy, but unfortunately, the patient pays a high price as ileostomy is necessary.

While the cause of ulcerative colitis is unknown several lines of evidence suggest that one or more metabolic by-products secreted by bacteria endogenous to the gut may be responsible. The theory that bacteria are involved has its roots in epidemiological studies which have linked colon cancer to ulcerative colitis. For example, work by Greenstein et al in *Gastroenterology,* Vol. 77, p. 290 (1979), shows that a high percentage of patients that suffer from ulcerative colitis subsequently develop colon cancer. Because of the association of colon cancer and ulcerative colitis it is probable that both diseases are caused by the same or similar bacterial metabolic by-products.

As discussed by Hill in *Cancer,* Vol. 36, p. 2387 (1975), colon cancer is thought to be due to metabolic conversion of bile acids into carcinogens by bacteria as the bile acids pass through the colon. The link between bile acids and colon cancer is supported by the observation that the risk of developing colon cancer is greater in people that ingest large amounts of fats. Excessive fat, as discussed by Howell in *J. Chronic Dis.,* Vol. 28, p. 67 (1975), stimulates the production and subsequent secretion of bile acids into the gut. The chemical reactions necessary to carry out the conversion of bile acids into potential carcinogens are known, and have been described by Hill in *Cancer,* Vol. 36, p. 2387 (1975), and Goddard et al in *J. Med. Microbiol.,* Vol. 8, p. 429 (1975). These reactions require an electron acceptor, and as noted by Goddard et al in *J. Med. Microbiol.,* Vol. 8, p. 429 (1975), the likely candidate in the colon is Vitamin K. Thus, it should be possible to prevent both ulcerative colitis and colon cancer by administering to patients drugs that antagonize the effects of Vitamin K.

SUMMARY OF THE INVENTION

According to the present invention a method is described for treating and/or preventing ulcerative colitis involving administering to a patient drugs drawn from a group that are biological antagonists of Vitamin K, particularly derivatives of $\alpha$, $\beta$, $\gamma$, and $\delta$ tocopherol. The drugs are administered in doses of 1-6 grams per day with one third of the dose being taken with each meal.

DETAILED DESCRIPTION OF THE INVENTION

Chemical antagonists of Vitamin K, particularly derivatives of tocopherols, have a surprising property that when administered to individuals suffering from ulcerative colitis cause a marked reduction in the symptoms of the disease. The use of the word "tocopherol" is used broadly to mean $\alpha$, $\beta$, $\gamma$ and $\delta$ tocopherol, structurally related molecules and their stereoisomers. These substances occur in nature and most frequently are associated with plants. Illustrative of a molecule derived from he tocopherols that has vitamin K antagonistic activity is $\alpha$-tocopherol quinone. Closely related compounds, such as $\beta$-, $\gamma$- and $\delta$-tocopherol quinone (and the quinones of the corresponding tocotrienols) should also possess vitamin K antagonistic activity since the active portion of the molecules have very similar structures. Moreover tocopherol is taken to include metal salts thereof, particularly physiologically acceptable ones such as sodium or potassium. Lastly, it would be easily ascertainable to those skilled in the art that synthetic homologues of tocopherol, specifically those that have modifications in the hydrocarbon tail and/or ring structures will yield molecules with altered antiulcerative colitis activity.

A large variety of vitamin K antagonist exist that are structurally unrelated to the tocopherols. Examples are coumarin or derivatives thereof, and warfarin. It will be apparent to those skilled in the art that these chemicals will have antiulcerative colitis activity.

It is to be anticipated that the subject invention method of treating ulcerative colitis will also be applicable to controlling and/or preventing cancer of the colon as the latter disease, as shown by Devroede et al in the *New England J. of Medicine,* Vol. 285, p. 17 (1971), is statistically linked with high probability to the former.

One embodiment of the invention is ingestion with each meal of a physiologically acceptable oxidizing agent, particularly ferrous gluconate, and tocopherol. The former oxidizes the latter in the gut to yield the antiulcerative colitis active agent. Within several days there is a marked reduction in the severity of the symptoms associated with ulcerative colitis; that is, little or no blood is present in the stool, and the frequency and intensity of cramps is reduced. Omission of either the oxidizing agent or tocopherol for only a few days causes the reappearance of symptoms. It is believed that the oxidizing agent oxidizes tocopherol to one or more oxidation products, particularly $\alpha$-tocopherolquinone. The latter is thought to be responsible for controlling the disease.

A second embodiment of the invention is administering a mixture of tocopherol derivatives, preferably orally either in pill or tablet form. The mixture is produced by oxidizing tocopherols obtained from vegetable oil, obtained from Frazier Farms as Vitamin E, in absolute alcohol at 40°-80° C. for 15-60 minutes, followed by extraction with an organic solvent, particularly diethyl ether, and washing the organic layer with an aqueous solution. Subsequently alcohol was added, the organic layer removed by evaporation, and water added to separate out the final product. About 1-6 grams per day of material was taken daily, one third of the dose being given orally with each meal. While all the doses are active in alleviating the symptoms of ulcerative colitis, the preferred dose is 3 grams per day. At this dose symptoms are not apparent. Discontinuation of the drug mixture causes a reappearance of symptoms within 2-3 days.

It will be obvious to those with ordinary skill in the art that by oxidizing a mixture of α, β, γ, and δ tocopherols to the corresponding α, β, γ, and δ tocopherolquinones, that most if not all of these, but particularly α-tocopherolquinone, contribute to controlling the disease, and that their degree of effectiveness parallels their Vitamin K antagonistic activity.

To facilitate or insure daily administration, the drug may be incorporated into liquid or solid edibles. Moreover, since the site of action of the drug's vitamin K antagonistic activity is believed to be against bacteria in the gut, the effaciousness of such compounds can be improved by derivatizing them as described by Drasar and Hill in *Human Intestinal Flora*, Academic Press (1974), so as to retard their absorption across the gut and thereby ensure that a high concentration of the drug is maintained in the gut.

Lastly, it is to be anticipated that variations in the amount of fat in the diet of ulcerative colitis patients may affect the degree of benefit achieved by the subject invention. High fat diets act to stimulate the secretion into the gut of bile compounds that are believed to be the substrates converted by bacteria into ulcerative colitis active agents. Thus, low fat diets will enhance the effect of the invention while high fat diest may be detrimental.

There have been disclosed below three forms of the best embodiments of the invention presently contemplated. However, it is to be understood that various changes and modifications may be made thereto without departing from the spirit of the invention.

EXAMPLE I

One method of treating ulcerative colitis is to administer physiologically acceptable oxiding agents and tocopherol such that the former oxidizes the latter in the gut to yield the active substance. A human white 60-kilogram male, 34 years old, with a chronic history of ulcerative colitis for 8 years, was the test subject. He presented chronic bloody diarrhea, severe facial rash and scalp lesions, and intense cramps and arthritis. A therapeutic regime was undertaken consisting of ingesting 650 mg of ferrous gluconate, and 1,000 IU of tocopherol three times a day with one third of the dose being taken with each meal. Within 2-3 days there was a progressive decrease in the severity of the symptoms, and by the end of one week there was significant remission of all symptoms. After 20 months of this regime the disease had stabilized to occasional bloody diarrhea, moderate rash and scalp lesions, mild arthritis and mild abdominal cramping. Ingestion of either ferrous gluconate or tocopherol alone had no effect; moreover, after treatment had begun and a remission of the disease established, omitting either or both chemicals caused a resumption of bleeding and subsequent reappearance of the facial rash and cramps.

EXAMPLE II

Once it was apparent that the oxidation of tocopherols in vivo was responsible for producing the antiulcerative colitis active agent, an effective and efficient method of synthesizing tocopherols was developed. The procedure developed involves dissolving in absolute ethanol 6 grams of a mixture of tocopherols obtained from vegetable oil which was purchased commercially from a Frazier Farms supermarket under the label of vitamin E. While a chemical analysis was not performed to determine the amount of α, β, γ, and δ tocopherols present in the vegetable oil, such preparations routinely are predominantly α-tocopherol with lesser amounts of β-, γ-, and δ-tocopherols. This material was dissolved in 600 mL of absolute ethanol, followed by the addition of 12 grams of $FeCl_3 \cdot 6H_2O$. The solution was heated for 40 minutes at 60° C. and diluted with water and extracted with diethyl ether. The organic layer was washed repeatedly with water after which 80 mL of absolute ethanol were added and ether removed by evaporation under atmospheric pressure. Lastly, water was added dropwise to the remaining solution until a golden yellow oil formed. This material is predominantly α-tocopherolquinone with lesser amounts of the other tocopherol derivatives being present.

EXAMPLE III

A second method of practicing the invention is to perform the oxidation of tocopherols in a laboratory, and administer the products rather than perform the oxidation in vivo. Again the test subject was a white 34-year old 60-kilogram male suffering from ulcerative colitis with symptoms consisting of frequent attacks of bloody diarrhea, moderate facial rash and scalp lessions, severe arthritis in his right hip, right knee and lower back, and severe abdominal cramping. Colonoscopy revealed the extension of inflammation and pseudopolyposis encompassing the entire descending and sigmoid colon. A therapeutic regime of oral ingestion of tocopherols derivatives produced as described in Example II was followed. Various doses were ingested daily for different periods of time with one third being taken at each meal, and their effect monitored. Table I shows that a marked remission of symptoms is apparent in the range of 0.6–0.9 grams per day, with maximum improvement at a dose of 3 grams per day. At the latter concentration there is neither bloody diarrhea, arthritis, nor scalp lesions or cramps. The only vestige of the disease is a mild facial rash. If the therapy is discontinued within 24 hours symptoms begin to reappear.

TABLE 1

Change in Patient Condition with Increasing Dose of α-Tocopherolquinone.

| | \multicolumn{11}{c}{Days on indicated dose} |
| --- | --- | --- | --- | --- | --- | --- | --- | --- | --- | --- | --- |
| | 0 | 6 | 7 | 20 | 10 | 17 | 15 | 7 | 6 | 8 | 9 | 37 |
| α-TQ (g/day) | — | 0.09 | 0.3 | 0.3 | 0.6 | 0.9 | 1.2 | 1.5 | 1.8 | 2.1 | 2.4 | 3.0 |
| Hgb (g/dl) | 10.1 | 10.3 | 11.0 | 11.9 | 11.1 | 11.7 | 12.3 | 12.4 | 11.8 | 11.1 | 11.6 | 14.3 |
| Hct (%) | 32.0 | 32.0 | 35.0 | 37.0 | 37.0 | 37.0 | 39.0 | 39.0 | 37.0 | 36.0 | 37.0 | 44.0 |
| Segs (%)[a] | 46 | 32 | 71 | 50 | 21 | 29 | 55 | 33 | 42 | 53 | 46 | 54 |
| Bands (%)[b] | 0 | 17 | 3 | 12 | 31 | 10 | 0 | 25 | 14 | 0 | 0 | 0 |
| Protein (g/dl)[c] | 4.2 | — | 4.6 | 5.0 | 4.9 | 5.0 | 5.1 | 5.3 | 5.0 | 5.1 | 5.0 | 5.5 |
| Prothrombin[d] time ratio | 1.0 | 1.1 | 1.0 | 1.0 | 1.0 | 1.0 | 1.0 | 1.0 | 1.0 | 1.1 | 1.0 | 1.0 |

TABLE 1-continued

Change in Patient Condition with Increasing Dose of α-Tocopherolquinone.

| | Days on indicated dose | | | | | | | | | | | |
|---|---|---|---|---|---|---|---|---|---|---|---|---|
| | 0 | 6 | 7 | 20 | 10 | 17 | 15 | 7 | 6 | 8 | 9 | 37 |
| Liver enzymes[e] | N | N | N | N | N | N | N | N | N | N | N | N |
| Stools/day | 6-8 | 6-8 | 4-6 | 4-6 | 4-6 | 4-6 | 4-6 | 3-4 | 3-4 | 3-4 | 3-4 | 3 |
| Stool blood | ++ | ++ | + | + | 0 | 0 | 0 | 0 | 0 | 0 | 0 | 0 |
| Arthritis | ++++ | ++++ | ++++ | +++ | +++ | ++ | + | + | + | + | + | 0 |
| Facial rash | ++ | ++ | ++ | ++ | + | + | + | + | + | + | + | + |
| Scalp lesions | ++ | ++ | + | + | + | 0 | + | + | + | 0 | 0 | 0 |
| Cramps | ++++ | ++++ | ++ | + | + | + | + | + | + | + | 0 | 0 |

[a]Segmented neutrophils.
[b]Band neutrophils.
[c]Total serum protein.
[d]Patient/Control.
[e]SGPT, SGOT, LDH, and alkaline phosphate.
N = normal.

We claim:

1. A method of preventing and/or treating ulcerative colitis comprising administering to a patient 1.5–6 grms daily of alpha, beta, gamma or delta tocopherol quinone.

2. A method of preventing and/or treating ulcerative colitis in patients comprising administering to a patient suffering from said ulcerative colitis 1.5–6 grms daily of alpha tocopherol quinone.

* * * * *